(12) United States Patent
Kuehnert et al.

(10) Patent No.: US 8,491,575 B2
(45) Date of Patent: Jul. 23, 2013

(54) APPARATUS FOR GENERATING A CORRECTING CUT SURFACE IN THE CORNEA OF AN EYE SO AS TO CORRECT AMETROPIA AS WELL AS A CONTACT ELEMENT FOR SUCH APPARATUS

(75) Inventors: Juergen Kuehnert, Jena (DE); Martin Wiechmann, Jena (DE); Michael Bergt, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 1106 days.

(21) Appl. No.: 12/514,757

(22) PCT Filed: Nov. 14, 2007

(86) PCT No.: PCT/EP2007/009849
§ 371 (c)(1),
(2), (4) Date: May 13, 2009

(87) PCT Pub. No.: WO2008/064771
PCT Pub. Date: Jun. 5, 2008

(65) Prior Publication Data
US 2010/0049174 A1 Feb. 25, 2010

Related U.S. Application Data

(60) Provisional application No. 60/867,913, filed on Nov. 30, 2006.

(30) Foreign Application Priority Data

Nov. 30, 2006 (DE) .......................... 10 2006 056 711

(51) Int. Cl.
*A61F 9/009* (2006.01)
*A61B 18/20* (2006.01)
(52) U.S. Cl.
USPC ............................................................ 606/4

(58) Field of Classification Search
USPC ................ 606/4–6, 10–13, 17; 359/290, 291, 359/298, 315, 318
See application file for complete search history.

(56) References Cited

U.S. PATENT DOCUMENTS

| 4,964,717 A | * | 10/1990 | Koester .................... 351/219 |
| 5,141,506 A | | 8/1992 | York |
| 5,324,281 A | | 6/1994 | Muller |

(Continued)

FOREIGN PATENT DOCUMENTS

| GB | 2 252 249 A | 8/1992 |
| WO | WO 2005/079717 A1 | 9/2005 |
| WO | WO 2006/058443 A1 | 6/2006 |

OTHER PUBLICATIONS

EyeQ Report, Ophthalmic Business Intelligence, No. 9, Nov. 22, 2006 (10 pgs.).

*Primary Examiner* — Ryan Severson
*Assistant Examiner* — Rachel S Papeika
(74) *Attorney, Agent, or Firm* — Christensen Fonder P.A.

(57) ABSTRACT

An apparatus for generating a correcting cut surface in the cornea including a laser unit, which can focus and move pulsed laser radiation; a first contact element; and a control unit, controlling the laser unit which has a standard setting which, when a standard curvature is imposed upon corneal surface by the first contact element, would lead to a standard cut surface. The standard cut surface has a known curvature with respect to a reference surface. The curvature, with respect to the reference surface of the correcting cut surface to be generated deviates from the known curvature of the standard cut surface. The apparatus includes a second contact element adapted to generate the correcting cut surface, which cornea imposes an actual curvature deviating from the standard curvature, thus generating a cut surface using the standard setting results in the correcting cut surface to be generated.

28 Claims, 4 Drawing Sheets

U.S. PATENT DOCUMENTS

| | | |
|---|---|---|
| 5,423,801 A | 6/1995 | Marshall et al. |
| 5,507,741 A | 4/1996 | L'Esperance, Jr. |
| 6,019,472 A * | 2/2000 | Koester et al. ............... 351/219 |
| 6,325,792 B1 | 12/2001 | Swinger et al. |
| 6,494,878 B1 | 12/2002 | Pawlowski et al. |
| 2004/0002694 A1 | 1/2004 | Pawlowski et al. |
| 2005/0143718 A1 | 6/2005 | Rathjen |
| 2007/0179478 A1 | 8/2007 | Dobschal et al. |

* cited by examiner

APPARATUS FOR GENERATING A CORRECTING CUT SURFACE IN THE CORNEA OF AN EYE SO AS TO CORRECT AMETROPIA AS WELL AS A CONTACT ELEMENT FOR SUCH APPARATUS

PRIORITY CLAIM

The present application is a National Phase Entry of PCT Application No. PCT/EP2007/009849, filed Nov. 14, 2007, which claims priority to U.S. Provisional Application No. 60/867,913, filed Nov. 30, 2006, and German Application Number 102006056711.0, filed Nov. 30, 2006, the disclosures of which are hereby incorporated by reference herein in their entirety.

FIELD OF THE INVENTION

The invention relates to an apparatus for generating a correcting cut surface in the cornea of an eye so as to correct ametropia, said apparatus comprising a laser unit, which can focus and move pulsed laser radiation in the cornea to generate a cut surface; a first contact element; and a control unit, which controls the laser unit to generate said cut surface and has a standard setting which, when a standard curvature is imposed upon the anterior corneal surface by the first contact element, leads in the cornea to a standard cut surface having a known curvature with respect to a reference surface. Further, the invention relates to a contact element for such apparatus.

BACKGROUND OF THE INVENTION

Such apparatus can be used in refractive ophthalmology for correction of the eyesight defect to cut a corneal lamella, which can be unilaterally detached from the corneal surface and folded aside. In this case, such apparatus is frequently referred to also as a laser keratome, which is used in the so called LASIK operation (laser in situ keratomileusis) to expose the corneal tissue by cutting the above-described corneal lamella (which is also called a flap).

In the LASIK operation, a defined corneal volume is then ablated, after cutting and folding open the flap, by means of an excimer laser, which is a different laser than the one used for cutting the flap. Subsequently, the flap is folded back down so that the profile of the anterior corneal surface is altered due to the removed corneal tissue according to the desired correction of ametropia.

On the one hand, such an approach for correction of ametropia leads to the use of two different lasers. On the other hand, the control of the excimer laser to remove the cornea is difficult and has to be carried out with extremely high precision.

In view thereof, it is the object of the invention to provide an apparatus for generating a correcting cut surface in the cornea of an eye so as to correct ametropia, by which apparatus the desired correcting cut surface can be easily achieved with high precision.

The object is achieved by an apparatus for generating a correcting cut surface in the cornea of an eye so as to correct ametropia, said apparatus comprising a laser unit, which can focus and move pulsed laser radiation in the cornea to generate a cut surface; a first contact element; and a control unit, which controls the laser unit to generate a cut surface and which has a standard setting which, when a standard curvature is imposed upon the anterior corneal surface by the first contact element, would lead to a standard cut surface in the cornea having a known curvature with respect to a reference surface, wherein the curvature, with respect to the reference surface, of the correcting cut surface to be generated deviates from the known curvature of the standard cut surface which can be generated, and said apparatus comprises a second contact element adapted to generate the correcting cut surface, which second contact element, when in contact with the anterior corneal surface, imposes upon the latter an actual curvature deviating from the standard curvature, and thus has the effect that generating a cut surface using the standard setting results in the correcting cut surface to be generated.

Thus, in the apparatus according to the invention, a cut surface is generated using the standard setting of the control unit, which facilitates operation of the apparatus. Determination of the profile of the correcting cut surface is realized by the individually adapted second contact element. Therefore, it is only required to adapt the contact element in accordance with the correcting cut surface to be generated for the desired correction of ametropia.

In particular, this enables the use of a conventional laser keratome for flap-cutting in order to generate the correcting cut surface, without requiring any change in the control of the laser unit. It is only required to provide the correspondingly adapted second contact element which imposes the actual curvature upon the anterior corneal surface.

The reference surface, is, for example, the surface which coincides with the anterior corneal surface before the cut surface is generated, in which case the cornea is not in contact with any of the contact elements and has its natural profile.

The second contact element may be provided such that, due to the imposed actual curvature alone, it has the effect that generating the cut surface using the standard setting results in the correcting cut surface to be generated. Thus, due to the imposed actual curvature, the cornea is deformed such that the standard cut surface coincides with the correcting cut surface to be generated. Such second contact element is particularly easy to produce.

In particular, the second contact element and/or the first contact element may have a refractive index adapted to the refractive index of the eye's cornea.

The second contact element, however, can also be provided such that the second contact element has a further optical property which also contributes to generating the correcting cut surface. Said property may be, for example, refraction and/or diffraction.

The second contact element can be provided such that the deviation between the actual curvature given by the second contact element and the standard curvature given by the first contact element corresponds to the deviation between the correcting cut surface and the standard cut surface. Such a contact element is easy to produce. The first contact element, for example, may comprise a spherically curved contact surface and the standard setting may be such that a flap having a constant thickness relative to the anterior corneal surface can be generated using the first contact element.

The second contact element may have a one-part design. However, it is also possible for the second contact element to comprise a main part, having a first contact surface, and an adapting element, which is connected with the first contact surface and comprises a second contact surface facing away from the first contact surface, the spatial shape of said second contact surface being selected such that the actual curvature can be imposed upon the cornea.

Due to this two-part design, particularly the main part of the second contact element can be used several times and the adaptation can be effected exclusively via said adapting element.

The main part may have the same design as the first contact element.

The adapting element may be provided as a sheet or a lens, which may be, for example, preformed sheets or lenses. It is also possible to individually adapt the sheets or lenses, respectively.

The correcting cut surface may be selected such that a corneal flap is separated from the cornea thereby, so that the curvature of the anterior corneal surface is modified accordingly.

It is also possible for the correcting cut surface to separate one side of a corneal lenticle (small corneal volume) from the surrounding corneal material. In this case, a further cut surface is generated, using the standard setting, by means of the apparatus and the first contact element or a further contact element contacting the anterior corneal surface, so as to generate a further correcting cut surface within the cornea, which, together with the correcting cut surface generated with the second contact element, completely separates the corneal lenticle from the surrounding cornea.

According to this approach, it is preferred to first generate the correcting cut surface located at a greater depth (i.e. at a greater distance from the anterior corneal surface). In particular, the correcting cut surface located at a greater depth may have a curvature relative to the anterior corneal surface, differing from that of the anterior corneal surface. The correcting cut surface located higher up may be provided, in particular, as a flap at a constant distance from the anterior corneal surface.

The apparatus may further comprise at least a third contact element, which imposes a further curvature upon the anterior corneal surface when contacting the latter, said further curvature deviating from the standard curvature as well as from the actual curvature of the second contact element, and thus has the effect that a cut surface generated using the standard setting results in a further correcting cut surface.

Further, the contact surface of the corresponding contact element defining the actual curvature may be flexible. Said flexibility is selected such that, although on average the actual curvature is imposed upon the anterior corneal surface, minor irregularities can be compensated for. This has the advantageous effect that the correcting cut surface to be generated has an extremely smooth profile. Said flexibility may be achieved, for example, by a thin, flexible layer (e.g. a gel layer) forming the contact surface, which is in turn applied to a contact element carrier that is rigid with respect to the cornea.

The contact elements may be made, for example, from glass or plastics.

The correcting cut surface may serve to correct myopia, hyperopia or other eyesight defects.

Further, a contact element for an apparatus for generating a correcting cut surface in the cornea of an eye so as to correct ametropia is provided, said apparatus comprising a laser unit which can focus and move pulsed laser radiation in the cornea to generate a cut surface; a standard element, and a control unit, which controls the laser unit to generate a cut surface and which has a standard setting which, when a standard curvature is imposed upon the anterior corneal surface by the standard element, would lead in the cornea to a standard cut surface having a known profile relative to a reference surface, wherein the curvature, with respect to the reference surface, of the correcting cut surface to be generated deviates from the known curvature of the standard cut surface which can be generated, and wherein the contact element, when contacting the anterior corneal surface, imposes upon the latter an actual curvature deviating from the standard curvature and, thus, has the effect that generating a cut surface by means of the apparatus using the standard setting results in the correcting surface to be generated.

For example, such a contact element allows to generate the desired correcting cut surface by means of a conventional laser keratome, without having to modify the control of the laser unit. It is only required to replace the standard element with the contact element according to the invention. Thus, the curvature of the correcting cut surface is given by the individually adapted contact element.

In particular, the contact element has the effect that, due to the imposed actual curvature alone, the cut surface generated using the standard setting results in the correcting cut surface to be generated. Such a contact element is particularly easy to produce.

Thus, the deviation between the actual curvature given by the contact element and the standard curvature given by the standard element may correspond to the deviation between the correcting cut surface and the standard cut surface. The contact element may have a one-part design. It may consist of transparent glass or transparent plastics. In particular, the refractive index of the contact element is adapted to the refractive index of the cornea.

As an alternative, the contact element may comprise a main part having a first contact surface and an adapting element, which is connected with said first contact surface and comprises a second contact surface facing away from the first contact surface, the spatial shape of said second contact surface being selected such that the actual curvature can be imposed upon the cornea. The adapting element may be provided as a sheet or as a lens. In such a two-part contact element, the main part, for example, may be re-used, in which case only the adapting element has to be replaced.

In the contact element, the contact surface defining the actual curvature can be flexible with respect to the cornea. However, said flexibility is selected such that on average the desired actual curvature can be imposed. This can be realized, for example, by providing the contact surface as a thin, flexible layer which is applied onto a rigid contact element carrier. Said flexible layer may be, for example, a gel layer. This flexibility allows compensation for minor irregularities in the cornea during contacting, so that the generated correcting cut surface has an extremely uniform profile without such irregularities.

In particular, a group of such described contact elements is provided, wherein all contact elements have a different design so as to allow different correcting cut surfaces to be generated.

Further, a method for producing a contact element as described above is provided, wherein the contact element is produced by material removal from a blank. Said material removal may be effected, for example, by means of diamond-turning, milling or ablation using laser radiation or by other methods. Of course, it is also possible to selectively apply or add material, respectively, to the blank so as to produce the contact element.

The blank may be, for example, a standard flap contact glass. Such standard flap contact glass may have, e.g. a spherically curved or a planar contact surface.

A contact element comprising the main part and the adapting element can be produced by mounting the adapting element to the main part. In particular, the second contact surface of the adapting element can be defined (e.g. by removing or applying material) before or after mounting to the main part.

There is further provided a method for generating a correcting cut surface in the cornea of an eye so as to correct ametropia by an apparatus comprising a laser unit, which can focus and move pulsed laser radiation in the cornea to generate a cut surface; a first contact element; and a control unit which controls the laser unit for generating a cut surface and comprises a standard control, which standard control would cause said standard cut surface in the cornea to have a known curvature with respect to a reference surface when a standard curvature is imposed upon the anterior corneal surface by the first contact element, wherein the curvature, with respect to the reference surface, of the correcting cut surface to be generated deviates from the known curvature of the standard cut surface which can be generated, and said method comprising the following steps: providing a second contact element adapted to generate the correcting cut surface; contacting the second contact element with the anterior corneal surface, whereby an actual curvature deviating from the standard curvature is imposed upon said surface, generating a cut surface using the standard setting, while the second contact element contacts the anterior corneal surface, in order to generate the correcting cut surface. This method allows to generate the desired correcting cut surface in a simple manner with great precision. In particular, a conventional laser keratome can be used to generate the correcting cut surface.

In the method, the second contact element may have the effect that, by the imposed actual curvature alone, the cut surface generated using the standard setting results in the correcting cut surface to be generated. Such contact element is particularly easy to produce. In particular, the second contact element can be provided such that the deviation between the actual curvature given by the second contact element and the standard curvature given by the first contact element corresponds to the deviation between the correcting and standard cut surfaces.

In particular, the second contact element can be provided as a one-part element. However, it is also possible for the second contact element to have a multi-part design. Thus, it may comprise a main part, having a first contact surface, and an adapting element, which is connected with the first contact surface and has a second contact surface facing away from the first contact surface and whose spatial shape is provided such that the actual curvature is imposed upon the anterior corneal surface.

In the method, the adapting element can be provided as a sheet or a lens.

Further, said method allows to separate a predetermined corneal lenticle within the cornea from the surrounding corneal tissue by generating a further correcting cut surface in addition to the generated correcting cut surface in that the anterior corneal surface is contacted by the first contact element or a third contact element, and then generation of a cut surface with the standard setting is carried out, in order to generate the further correcting cut surface. Both correcting cut surfaces together separate the volume of surrounding corneal tissue which corresponds to the corneal lenticle. The corneal lenticle is then removed from the cornea through an opening to the anterior corneal surface, such that both correcting cut surfaces contact each other and the anterior corneal surface thus has a modified curvature.

When generating the corresponding correcting cut surfaces in the cornea by the pulsed laser radiation, several processes initiated by the pulsed laser radiation take place in a time sequence within the tissue. If the power density of the radiation exceeds a threshold value during any pulse, an optical breakthrough forms which generates, for example, a plasma bubble in the cornea. The plasma bubble grows due to expending gas after the optical breakthrough has formed. If the optical breakthrough is not maintained, the gas generated in the plasma bubble is absorbed by the surrounding tissue and the bubble disappears again. Tissue-separating effects acting without a plasma bubble are also possible. For the sake of simplicity, all such processes, including their effects, are summarized herein by the term "optical breakthrough".

In order to separate tissue, the laser radiation is applied in pulsed form, with the pulse duration usually being less than 1 ps. Thus, the power density required for the respective pulse to initiate the optical breakthrough is achieved within a small spatial region. High focusing of the laser beam in combination with the short pulses allows to insert the optical breakthrough in the cornea with pinpoint accuracy. In order to generate a cut, a series of optical breakthroughs is generated at the locations predetermined by the standard setting in combination with the corresponding contact element such that the desired correcting cut surface is formed thereby.

It is evident that the features mentioned above and those mentioned below, which are yet to be explained, can be used not only in the combinations mentioned, but also in any other combinations, or alone, without departing from the scope of the present invention.

BRIEF DESCRIPTION OF THE DRAWINGS

The invention will be explained in more detail below, by way of example and with reference to the enclosed Figures, which also disclose essential features of the invention. In the drawings.

DETAILED DESCRIPTION

Figure 1:
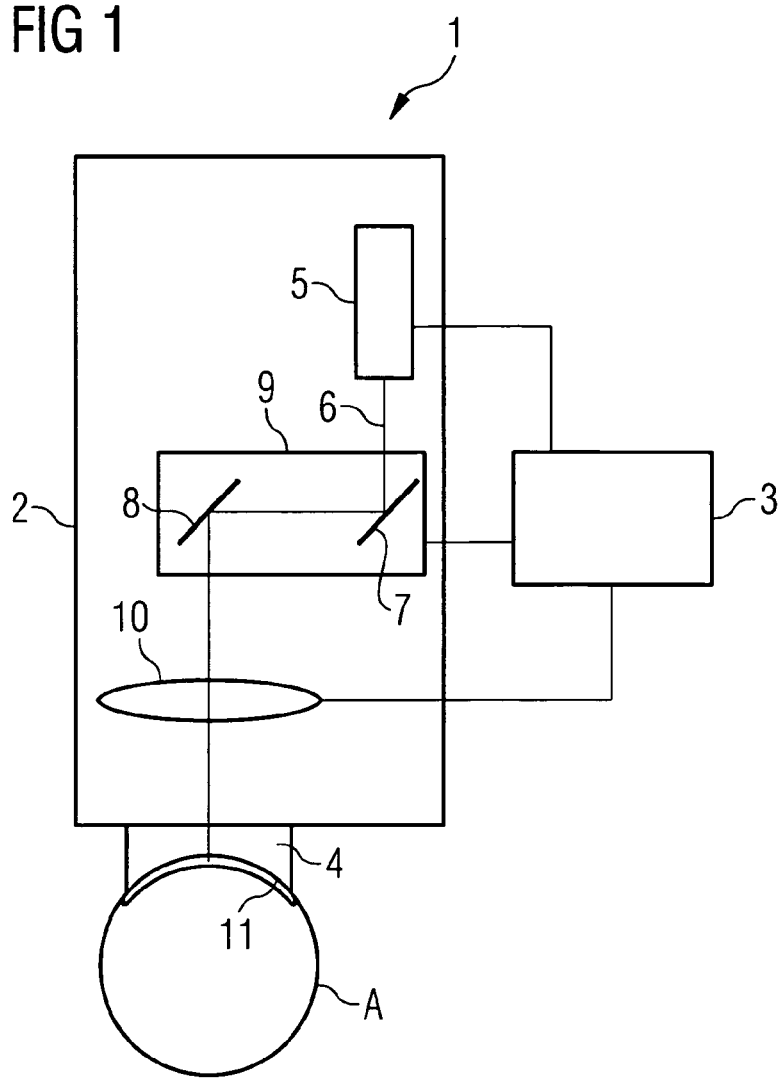
FIG. 1 is a schematic view of an embodiment of the correcting apparatus according to the invention.

In the embodiment shown in FIG. 1, the correcting apparatus 1 for generating a correcting cut surface in the cornea 11 of an eye A so as to correct ametropia comprises a laser unit 2, a control unit 3 for control of the laser unit 2, as well as a contact element 4 releasably coupled to the laser unit 2 and, as will be described below, specifically adapted for the respective correcting cut surface.

As is evident from the schematic representation of FIG. 1, the laser unit 2 comprises a laser 5 emitting pulsed laser radiation 6. The pulse duration is, for example, within the femtosecond range (e.g. 50 to 800 fs), with a pulse repetition rate of between 10 and 500 kHz.

The pulsed laser radiation is focused through the contact element 4 into the cornea of an eye A contacting the contact element 4, said focusing being effected by means of two deflecting mirrors 7, 8, which form a scanner 9, and by optics 10, and is moved within the cornea. This is done under the control of the control unit 3, so that basically any desired locations in the cornea can be exposed to the pulsed laser radiation 6.

Of course, the scanner can also be provided in a different manner known to the person skilled in the art.

The control unit 3 can control the laser unit 2 such that an optical breakthrough for separation of tissue is generated at the respective focus position in the cornea. The focus positions are selected to be adjacent each other such that a desired cut surface is present in the cornea.

The laser unit 2 and the control unit 3 are shown in a schematic and greatly simplified form in FIG. 1 and can be provided, for example, in the same manner as in a conventional laser keratome, which is used in the so-called LASIK method (laser in situ keratomileusis) to cut a thin lamella (often referred to also as flap) which is unilaterally detached from the cornea. Thus, the optics 10, for example, which are merely represented as a lens, can comprise several optical elements which are suitably arranged along the beam path from the laser 5 up to the contact element 4.

The laser unit 2 and the control unit 3 are provided such here in such a manner that they can cut a flap by means of a flap contact glass 12 (FIG. 2), which may be part of the apparatus 1, instead of the contact element 4 and using a standard setting of the control unit 3. The standard setting is defined here for the flap contact glass 12, whose side 13 facing the cornea 11 (referred to hereinafter as flap contact surface 13) is spherically curved, as is evident from the schematic representation of FIG. 2, which shows only the flap contact glass 12 as well as part of the cornea 11 of the eye A. The standard setting of the control unit 3 is adapted to the flap contact glass 12 and to the curvature imposed upon the anterior corneal surface 15 by the flap contact surface 13, such that the standard cut surface 14 shown by a dashed line in FIG. 2 can be generated. The standard cut surface 14 which can be generated is characterized here in that the distance D from the anterior corneal surface 15 is constant.

Of course, the flap contact glass 12 can be provided with a planar flap contact surface. In this case, the standard setting is selected such, for example, that the standard cut surface 14 which can be generated is at a constant distance D from the anterior corneal surface. However, the following description is based on the flap contact glass 12 comprising a spherically curved flap contact surface 13.

Figure 2:
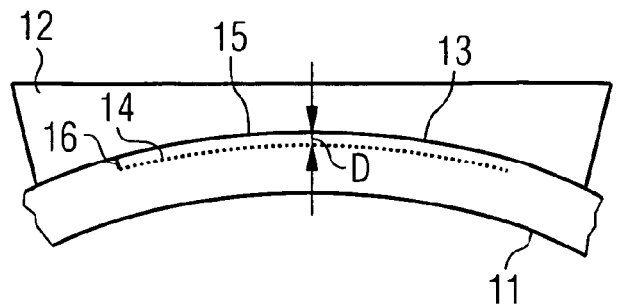
FIG. 2 is a schematic representation of a flap contact glass 12 in contact with the cornea 11.

In order to be able to lift the desired flap, the opening cut 16 shown in FIG. 2 and extending substantially perpendicular to the anterior surface 15 would also have to be generated. However, the following description is based on the standard setting of the control unit 3 for generating the standard cut surface 14, wherein the standard cut surface 14 is generated during a cutting operation once the anterior corneal surface 15 has the standard curvature predetermined by the side 13 of the flap contact glass 12.

Figure 3:
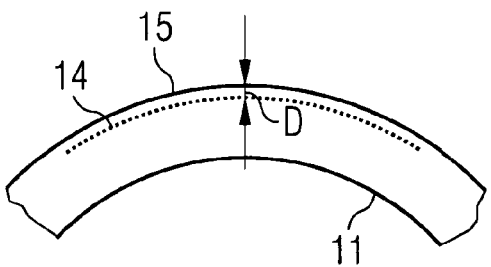
FIG. 3 is a schematic representation of the standard cut surface which can be generated in the cornea 11.

Therefore, FIG. 3 schematically shows the profile of only the standard cut surface which can be generated relative to the anterior corneal surface 15 with its natural curvature. The profile of the anterior corneal surface 15 with its natural curvature is referred to hereinafter as reference surface F.

The standard cut surface 14 described in connection with FIGS. 2 and 3, however, is not generated for the desired correction of defective eyesight (ametropia) and merely serves to characterize the standard setting of the control unit 3. This is because the correction of defective eyesight is achieved by generating a cut surface using the contact element 4 (FIG. 1) and the standard setting, as will be described hereinafter.

It is assumed that, for correction of defective eyesight, a corneal flap has to be separated from the cornea 11, such that the thus-modified curvature of the anterior corneal surface results in the desired correction of defective eyesight. The required separating cut surface is referred to here as correcting cut surface, with the profile of the distance between the correcting cut surface and the anterior corneal surface or the reference surface F, respectively, not being constant, but varying.

According to the invention, the contact element 4 (FIG. 4) is provided such that the curvature or the actual curvature, respectively, of the anterior corneal surface 15 is modified upon contact with the contact element 4 (FIG. 5) such that the correcting cut surface coincides with the cut surface 14 in the deformed cornea. This leads to the advantage that only the contact element 4 has to be adapted in order to generate the correcting cut surface 18 which differs from one patient to another. The laser unit 2 and the control unit 3 can always be operated using the standard setting.

Figure 4:
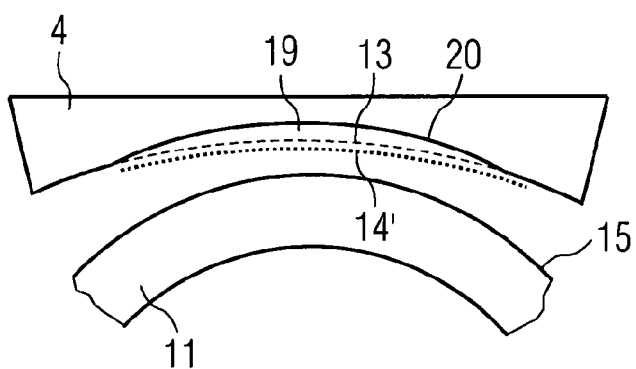
FIG. 4 is a schematic representation of a contact element 4 according to the invention.

FIG. 4 shows the adapted contact element 4 whose contact surface 20 facing the cornea 11 has a different curvature than the side 13 (shown by a dashed line in FIG. 4) of the flap contact glass 12. A dotted line in FIG. 4 represents the surface in which the laser radiation 6 is focused according to the standard setting in order to achieve a separation of tissue. Said surface is referred to hereinafter also as focus surface 14'.

Figure 5:
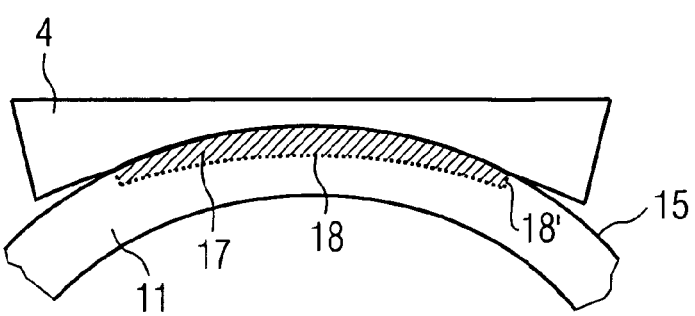
FIG. 5 depicts a representation of the contact element 4 of FIG. 4 in contact with the cornea 11.

FIG. 5 shows the cornea 11 in contact with the contact element 4. The contact element imposes upon the cornea 11 an actual curvature which is modified as compared to the standard curvature. In this condition, the cut is generated by means of the apparatus 1 using the standard setting, whereby the correcting cut surface 18 shown by a dotted line is generated. Further, a circumferential opening cut 18' is carried out, which extends substantially perpendicularly from the periphery of the correcting cut surface 18 to the anterior corneal surface 15. The opening cut 18' is carried out generally like the opening cut 16, although the opening cut 18', as seen in a top view of the anterior corneal surface 15, has a closed ring shape, such that the corneal flap 17, indicated by gray shading in FIG. 5, can be lifted off the remaining cornea 11.

Figure 6:
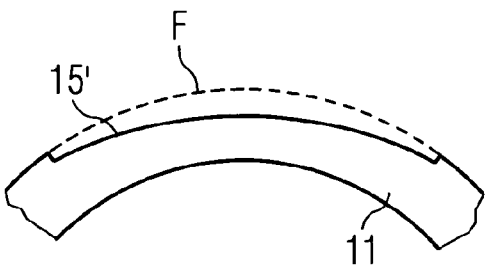
FIG. 6 depicts the cornea 11 after removal of the corneal flap 17 separated in the condition of FIG. 5.

After generating the correcting cut surface 18 shown in FIG. 5 as well as the opening cut 18', the contact element 4 is moved away from the cornea 11. Next, the corneal flap 17 is lifted completely so that the cornea returns to its original curvature, but without the removed corneal flap 17. As shown in FIG. 6, this leads to a modified curvature of the (new) anterior corneal surface 15' relative to the reference surface F shown by a dashed line. This modified curvature of the anterior corneal surface 15' should be achieved in order to correct the eyesight defect.

The opening cut 18' can be omitted, if the correcting cut surface 18 itself extends up to the anterior corneal surface 15, as will be described hereinafter, for example, in connection with FIGS. 11 to 13.

As a comparison between FIG. 6 and FIG. 3 shows, the curvature of the new anterior corneal surface 15' (FIG. 6) and, thus, also the curvature of the correcting cut surface 18 relative to the reference surface F differs from the curvature of the standard cut surface 14 with respect to the reference surface F (FIG. 3). It is evident, in particular, that the distance from the correcting cut surface 18 to the reference surface F varies over the correcting cut surface 18, whereby the modified curvature of the new anterior corneal surface 15' is achieved.

The adaptation of the correcting apparatus 1 to the particular correcting cut surface 18 to be generated respectively, which naturally depends on the respective correction of defective eyesight for each eye, is thus effected only by a suitable design of the contact element 4. No individual adaptation has to be carried out on the apparatus and, in particular, on the control of the laser unit 2 by means of the control unit 3, which considerably simplifies the generation of the desired correcting cut surface 18.

The contact element 4 can be produced, for example, by removing the corresponding region 19 (in FIG. 4, the region between the contact surface 20 and the flap contact surface 13, indicated by a dashed line) on the contact side 13 of a flap contact glass 12. Such material removal can be carried out by known methods, such as, for example, diamond-turning, milling or ablation by means of laser radiation.

The region 19 is selected such, on the basis of the flap contact glass 12 and the standard setting of the control unit 3, that the thickness profile between the contact surface 20 and the focus surface 14' corresponds to the thickness profile of the corneal flap 17 to be removed. The thickness profile of the corneal flap 17 can be computed, for example, using the same formulae and algorithms which are employed to compute the required removal of corneal material in photorefractive keratectomy (PRK).

Figure 7:
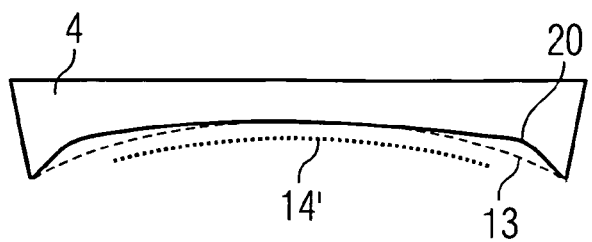
FIG. 7 is a schematic view of a further contact element according to the invention.

The contact element 4 shown in FIGS. 4 and 5 allows to correct myopia. FIG. 7 shows an example of the contact element 4 with a modified contact surface 20, which contact element serves to correct hyperopia and which can also be produced by material removal from a flap contact glass 12. The position of the flap contact surface 13 is indicated by a dashed line for comparison. Further, the focus surface 14' is indicated by a dotted line.

Of course, the contact elements 4 described so far need not be produced from a flap contact glass 12, for which the standard setting of the control unit is adapted. They can also be produced from any other contact element blank by material removal.

Figure 8:
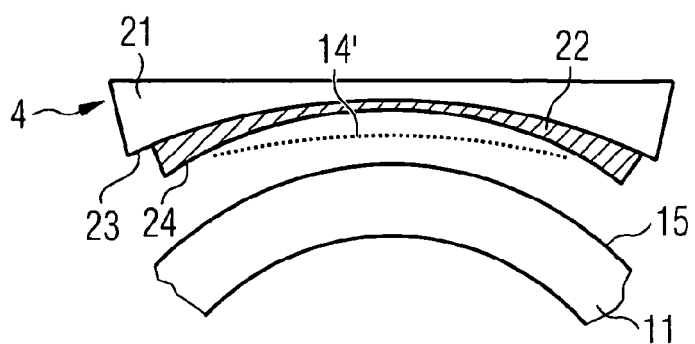
FIG. 8 is a schematic representation of a further contact element according to the invention.

The contact elements 4 described so far have all had a one-part design. FIG. 8 shows an example of a two-part contact element 4 which comprises a main part 21 as well as an adapting element 22. The main part 21 alone can be provided, for example, as a flap contact glass, with the corresponding focus surface 14' being represented by a dotted line, with the control unit 3 being set to its standard setting.

The adapting element 22 is mounted to the spherically curved lower side 23 of the main part 21. The thickness profile of the adapting element 22 is selected such that the contact element 4 shown in FIG. 8 can be used to correct myopia with the standard setting of the control unit 3.

Figure 9:
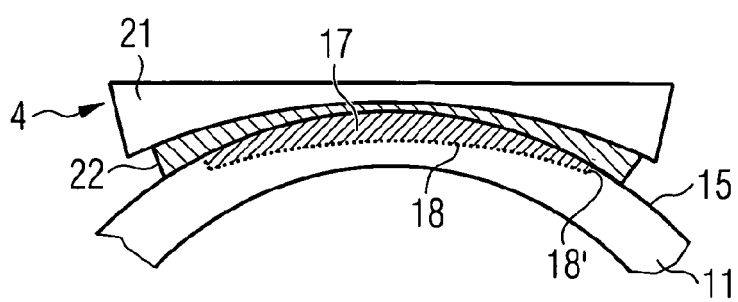
FIG. 9 is a schematic representation of the contact element 4 of FIG. 8 in contact with the cornea 11.
Figure 10:
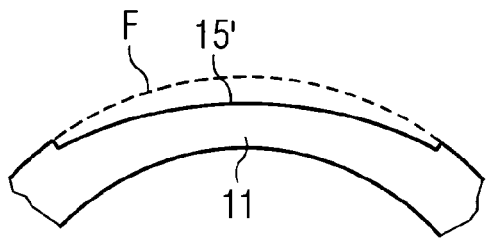
FIG. 10 is a schematic representation of the cornea 11 after removal of the corneal flap 17 separated in the condition of FIG. 9.

FIG. 9 shows the contact element 4 in contact with the cornea 11 such that the lower side 24 of the adapting element 22 imposes the desired actual curvature upon the cornea 11.

In this condition, the correcting cut surface 18 is generated by means of the laser unit 2 and the control unit 3, using the standard setting. Further, the opening cut 18' is generated in the same manner as in the embodiment described in connection with FIGS. 4 to 6. However, the opening cut 18' may be omitted, if the correcting cut surface 18 is led up to the anterior corneal surface 15, as will be described below, for example, in connection with FIGS. 11 to 13.

Thereafter, the contact element 4 is moved away from the cornea 11, so that the cornea 11 returns to its original curvature. However, the corneal flap 17 is removed, so that the modified anterior corneal surface 15' has the curvature, with respect to the reference surface F, required for correction of defective eyesight.

The adapting element 22 may be provided as a lens or sheet, in which case the thickness profile of the adapting element can be suitably adapted, if necessary, before or after being connected to the main part 21.

Figure 11:
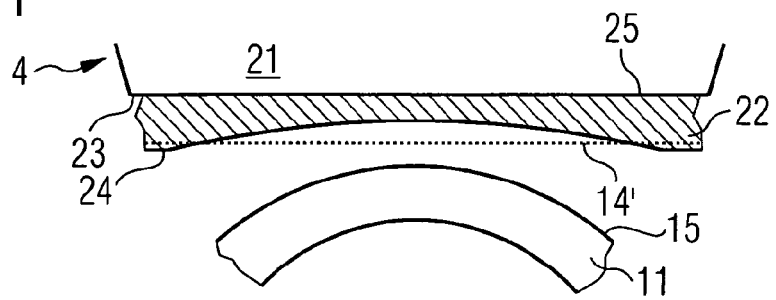
FIG. 11 is a schematic representation of a further contact element 4 according to the invention.
Figure 12:
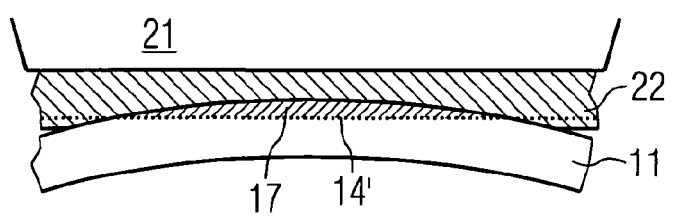
FIG. 12 is a schematic representation of the contact element 4 of FIG. 11 in contact with the cornea 11.
Figure 13:
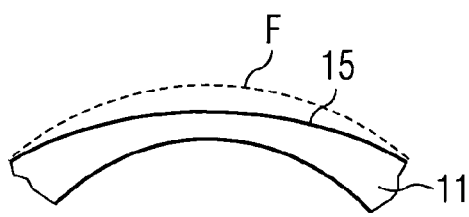
FIG. 13 is a schematic representation of the cornea after removal of the corneal flap 17 separated in FIG. 12.

FIGS. 11 and 12 show a different embodiment of a two-part contact element 4, in which embodiment the main part 21 has a planar lower side 23. The focus surface 14', which can be generated with respect to the main part 21, when the control unit 3 is set to its standard setting, is again represented by a dotted line. The adapting element 22, which is mounted to the lower side 23, comprises a planar upper side 25 which is connected with the lower side 23, as well as a concave lower side 24. This shows that the contact element 4 of FIG. 11 serves to correct myopia.

FIG. 12 shows the condition in which the contact element 4 contacts the cornea 11 and imposes upon the latter the actual curvature given by the geometrical shape of the lower side 24. In the case of a cut along the focus surface 14', the desired corneal flap 17 is cut away from the cornea, so that upon removal of the contact element 4 and the corneal flap 17, the (new) anterior corneal surface 15' has the profile, relative to the reference surface F, shown in FIG. 13. In this embodiment, the correcting cut surface extends up to the anterior corneal surface 15, so that no additional opening cut is necessary. This is achieved by the thickness of the adapting element 22 being greater in its outer peripheral region than the distance from the focus surface 14' to the lower side 23 in this region, so that the focus surface 14' laterally extends to the adapting element.

In connection with FIGS. 14 to 18, the steps will be described hereinafter by which the apparatus 1 of FIG. 1 can separate a corneal lenticle in the cornea 11 from the surrounding corneal material.

Figure 14:
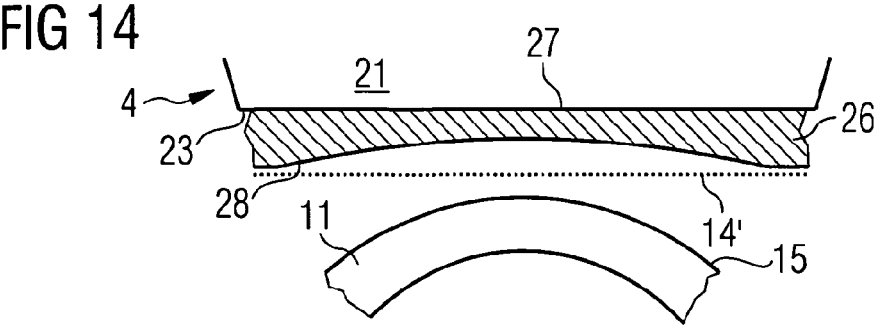
FIG. 14 depicts a contact element 4 according to a further embodiment.

As shown in FIG. 14, a two-part contact element 4 which comprises a main part 21, having a planar lower side 23, and a first adapting element 26 is provided again. The focus surface 14' for the main part 21 is represented as a dotted line, with the control unit 3 being set to its standard setting.

The upper side 27 of the first adapting element 26 is planar and is connected with the lower side 23 of the main part 21. The lower side 28 of the first adapting element is concave.

Figure 15:
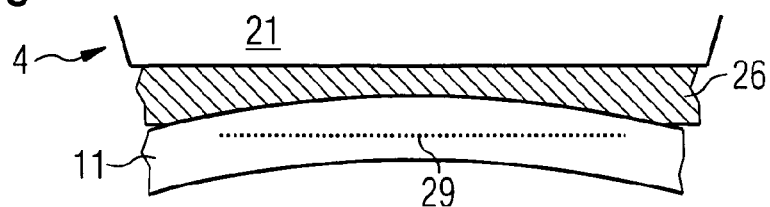
FIG. 15 depicts the contact element 4 of FIG. 14 in contact with the cornea 11.
Figure 16:
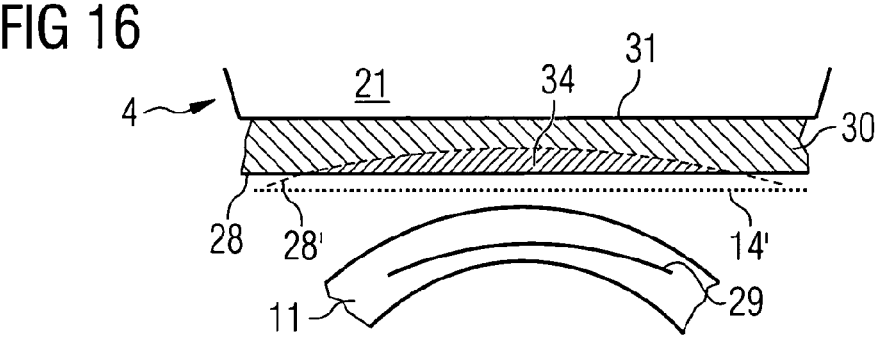
FIG. 16 depicts a contact element 4 according to a further embodiment.

FIG. 15 shows the contact element 4 in contact with the cornea 11 and imposing upon the latter the actual curvature defined by the lower side 28. By carrying out the cut using the standard setting, the first correcting cut surface 29 is generated in the cornea 11.

Next, the contact element 4 is moved away from the cornea 11, and the first adapting element 26 is removed from the main part 21. Instead, a second adapting element 30 having a planar upper side 31 is mounted to the lower surface 23 of the main part 21. The lower surface of the second adapting element 30 is also planar so that the second adapting element has a constant thickness. This contact element 4 is shown in FIG.

16, wherein the contour or the curvature of the lower surface 28 of the first adapting element 26 is also indicated by a dashed line 28'. The region between the dashed line 28' and the lower surface 33 defines the shape of the lenticle 34.

Figure 17:
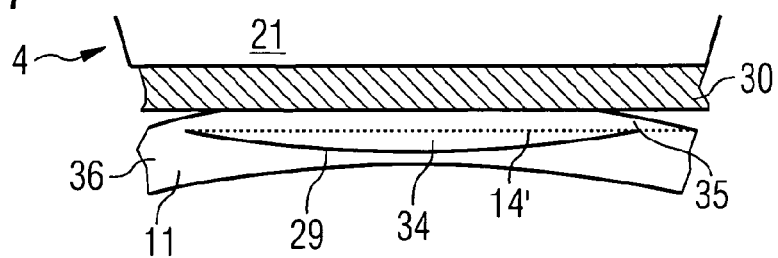
FIG. 17 depicts the contact element 4 of FIG. 16 in contact with the cornea 11.
Figure 18:
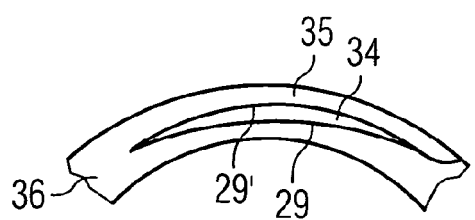
FIG. 18 depicts the profile of the correcting cut surfaces generated in the cornea 11 in the conditions of FIGS. 15 and 17.

FIG. 17 shows the condition in which the contact element 4 contacts the cornea 11 and imposes upon the anterior corneal surface 5 the actual curvature defined by the lower surface 32. Then, a cut is made along the focus surface 14', which cut not only confines the upper side of the lenticle here, but is also led laterally towards the right hand side in FIG. 17, so that the cut is led up to the anterior corneal surface 15. Thereby, a flap 35 is cut, which is not led up to the anterior corneal surface in the region 36 (left hand side of FIGS. 16 to 18), so that the region 36 serves as a hinge of the flap 35.

Then, the contact element 4 is removed from the cornea 11, so that both correcting cut surfaces 29 and 29' confine the desired lenticle 34 and separate it from the surrounding corneal material. The lenticle 34 can be removed after folding open the flap 35. The flap 35 is folded down again after that, so that the second correcting cut surface 29' comes to rest on the first correcting cut surface 29 and, thus, the anterior corneal surface 25 has a different (desired) curvature (not shown). Thus, the desired correction of defective eyesight is achieved.

It is advantageous for the first adapting element 26 to be thinner than the second adapting element 30, because the correcting cut surface located at a greater depth can thus be generated first. It is also advantageous to first generate the correcting cut surface having a curvature which deviates with respect to the reference surface F, in order to achieve optimal centering. Therefore, the flap 35 is generated by the second correcting cut surface 29' in the described embodiment.

In addition to the correction of myopia or hyperopia, other eyesight defects can also be corrected, of course. For example, astigmatism can be corrected. It is also possible, of course, to carry out corrections of a higher order.

The features of the above-described embodiments can be combined with each other where this makes sense.

The invention claimed is:

1. An apparatus for generating a correcting cut surface in the cornea of an eye so as to correct ametropia, said apparatus comprising:
a laser unit, that focuses and moves pulsed laser radiation in the cornea to generate a cut surface;
a first contact element with a standard curvature;
a control unit, which controls the laser unit to generate such a cut surface and which has a standard setting which, when the standard curvature is imposed upon the anterior corneal surface by the first contact element, leads to a standard cut surface in the cornea, said standard cut surface having a known curvature with respect to a reference surface, wherein the curvature of the correcting cut surface to be generated, with respect to the reference surface, deviates from the known curvature of the standard cut surface and
a second contact element adapted to generate the correcting cut surface;
which second contact element, when in contact with the anterior corneal surface, imposes upon the corneal surface an imposed actual curvature deviating from the standard curvature, and thus has the effect that generating a cut surface using the standard setting of the control unit results in the correcting cut surface to be generated.

2. The apparatus as claimed in claim 1, wherein the second contact element, due to the imposed actual curvature alone, has the effect that generating the cut surface using the standard setting results in the correcting cut surface to be generated.

3. The apparatus as claimed claim 1, wherein the second contact element is shaped such that the deviation between the actual curvature defined by the second contact element and the standard curvature defined by the first contact element corresponds to the deviation between the correcting and standard cut surfaces.

4. The apparatus as claimed in claim 1, wherein the second contact element has a one-part design.

5. The apparatus as claimed in claim 1, wherein the second contact element comprises a main part, having a first contact surface, and an adapting element, connectable with the first contact surface and comprising a second contact surface, which faces away from the first contact surface and whose spatial shape is selected such that the actual curvature can be imposed upon the cornea.

6. The apparatus as claimed in claim 5, wherein the adapting element comprises a sheet or lens.

7. The apparatus as claimed in claim 1, wherein the correcting cut surface and the standard cut surface are configured to separate a corneal lenticle from surrounding corneal tissue.

8. The apparatus as claimed in claim 1, wherein the second contact element comprises a contact surface defining the actual curvature which has a flexible design with respect to the cornea.

9. The apparatus as claimed in claim 1, further comprising at least a third contact element which, when in contact with the anterior corneal surface, imposes upon the anterior corneal surface a further deviation from the standard curvature that also deviates from the actual curvature of the second contact element and thus causes a cut surface generated using the standard setting to lead to a further correcting cut surface.

10. A contact element for an apparatus for generating a correcting cut surface in the cornea of an eye so as to correct ametropia, wherein said apparatus comprises:
a laser unit that focuses and moves pulsed laser radiation in the cornea to generate a cut surface;
a standard element; and
a control unit, which controls the laser unit to generate a cut surface and which has a standard setting which, when a standard curvature is imposed upon the anterior corneal surface by the standard element, leads to a standard cut surface in the cornea, said standard cut surface having a known curvature with respect to a reference surface, wherein the curvature, with respect to the reference surface, of the correcting cut surface to be generated deviates from the known curvature of the standard cut surface which can be generated, and the contact element, when in contact with the anterior corneal surface, imposes upon the anterior corneal surface an actual curvature deviating from the standard curvature, and thus has the effect that generating a cut surface using the standard setting results in the correcting cut surface being generated.

11. The contact element as claimed in claim 10, which, due to the imposed actual curvature alone, has the effect that generating the cut surface using the standard setting results in the correcting cut surface to be generated.

12. The contact element as claimed in claim 10, wherein the deviation between the actual curvature defined by the contact element and the standard curvature defined by the standard element corresponds to the deviation between the correcting and standard cut surfaces.

13. The contact element as claimed in claim 10, wherein the contact element has a one-part design.

14. The contact element as claimed in claim 10, wherein the contact element comprises a main part, having a first contact surface, and an adapting element, connectable with the first contact surface and a second contact surface, which faces away from the first contact surface and whose spatial shape is selected such that the actual curvature can be imposed upon the cornea.

15. The contact element as claimed in claim 14, wherein the adapting element comprises a sheet or a lens.

16. The contact element as claimed in claim 10, wherein the contact surface defining the actual curvature has a flexible design with respect to the cornea.

17. A group of contact elements as claimed in claim 10, each of said group of contact elements being designed differently from the other contact elements in the group to allow different correcting cut surfaces to be generated.

18. A method for producing the contact element as claimed in claim 10, further comprising producing the contact element from a blank by material removal.

19. A method for producing the contact element as claimed in claim 14, comprising producing the contact element by mounting the adapting element to the main part.

20. The method as claimed in claim 19, further comprising defining the shape of the second contact surface by material removal from the adapting element before mounting it to the main part.

21. The method as claimed in claim 19, further comprising defining the shape of the second contact surface by material removal from the adapting element after mounting it to the main part.

22. A method for generating a correcting cut surface in the cornea of an eye so as to correct ametropia, using an apparatus comprising a laser unit, that focuses and moves pulsed laser radiation in the cornea to generate a cut surface; a standard element; and a control unit, which controls the laser unit to generate a cut surface and which has a standard setting which, when a standard curvature is imposed upon the anterior corneal surface by the standard element, leads to a standard cut surface in the cornea, said standard cut surface having a known curvature with respect to a reference surface, wherein the curvature, with respect to the reference surface, of the correcting cut surface to be generated deviates from the known curvature of the standard cut surface which can be generated, the method comprising:

providing a second contact element adapted to generate the correcting cut surface;

contacting the second contact element with the anterior corneal surface, whereby an actual curvature deviating from the standard curvature is imposed upon said anterior corneal surface;

generating a cut surface using the standard setting, while the second contact element contacts the anterior corneal surface, in order to generate the correcting cut surface.

23. The method as claimed in claim 22, wherein the second contact element, due to the imposed actual curvature alone, has the effect that generating the cut surface using the standard setting results in the correcting cut surface to be generated.

24. The method as claimed in claim 22, further comprising providing the second contact element such that the deviation between the actual curvature defined by the second contact element and the standard curvature defined by the standard element corresponds to the deviation between the correcting and standard cut surfaces.

25. The method as claimed in claim 22, further comprising providing the second contact element such that it has a one-part design.

26. The method as claimed in claim 22, further comprising providing the second contact element such that the second contact element comprises a main part, having a first contact surface, and an adapting element, connected with the first contact surface and comprising a second contact surface, which faces away from the first contact surface and whose spatial shape is selected such that the actual curvature can be imposed upon the cornea.

27. The method as claimed in claim 26, further comprising providing the adapting element as a sheet or lens.

28. The method as claimed in claim 22, further comprising contacting the anterior corneal surface by the standard element or by a third contact element, and generating a cut surface using the standard setting to generate a further correcting cut surface which, together with the first correcting cut surface, separates a corneal lenticle from the surrounding cornea.

\* \* \* \* \*